United States Patent [19]

Royer

[11] 4,315,074
[45] Feb. 9, 1982

[54] MOLECULAR TRANSFORMATION PROCEDURE

[75] Inventor: Garfield P. Royer, Worthington, Ohio

[73] Assignee: Pierce Chemical Company, Rockford, Ill.

[21] Appl. No.: 51,229

[22] Filed: Jun. 22, 1979

Related U.S. Application Data

[60] Division of Ser. No. 907,503, May 19, 1978, Pat. No. 4,182,654, and a continuation-in-part of Ser. No. 680,462, Apr. 26, 1976, abandoned, which is a continuation-in-part of Ser. No. 507,198, Sep. 18, 1974, abandoned.

[51] Int. Cl.$^3$ .................. C12P 21/02; C12P 21/00
[52] U.S. Cl. .................. 435/70; 435/68; 260/112.5 R
[58] Field of Search .................. 260/112.5 R; 435/68, 435/272, 69, 70; 424/177

[56] References Cited

U.S. PATENT DOCUMENTS 3,386,888  6/1968  Chibata et al. .................. 195/2
3,753,970  8/1973  Bouchauden et al. ........ 260/112.5 R
3,814,732  6/1974  Wang .................. 260/112.5 R
3,849,390  11/1974 McGregor et al. .......... 260/112.5 R
3,948,821  4/1976  de Benneville .............. 260/112.5 R
3,951,741  4/1976  Pfaender et al. .................. 195/29

OTHER PUBLICATIONS

Ohno et al., J. Am. Chem. Soc., vol. 92, pp. 4098-5000, 1970.
Blecher et al., Liebigs Ann. Chem., 1973, 1263-1268.
Myers et al., Peptides, Chemistry, Structure and Biology, Proceedings of American Peptide Symposium IV, pp. 325-327, 1976.
Chemical Abstracts, vol. 85, No. 23, Abstract No. 177910c, p. 573, Meyers et al., "Enzymes as Reagents in Peptide Synthesis", 1976.
Chemical Abstracts, vol. 84, No. 7, Abstract No. 44649g, p. 555, "Novel Use of Enzymes as Reagents in Peptide Synthesis. Enzymic Removal of Amine Protecting Groups", Meyer, 1976.
Chemical Abstracts, vol. 83, No. 14, p. 608, abstract no. 114896y, Meyers, "Enzymes as Reagents in Peptide Synthesis. Enzymic Removal of Amine Protecting Groups", 1975.

Primary Examiner—Blondel Hazel

[57] ABSTRACT

A process is disclosed for synthesizing a peptide chain involving reacting, in aqueous solution, an amino acid containing a blocked alpha amino or carboxyl group with a polynucleotide handle to form a covalently bonded complex. The complex is separated from unreacted acid by reversible coupling to a complementary polynucleotide adsorbent immobilized on an insoluble support, and then the complex is eluted from the support as an aqueous solution. The complex is then enzymatically deblocked and used as the precursor for repeating the reaction with a further acid and the process reiterated. During the process, those chains which failed to react with a given acid can be removed by enzymatic degradation.

12 Claims, 1 Drawing Figure

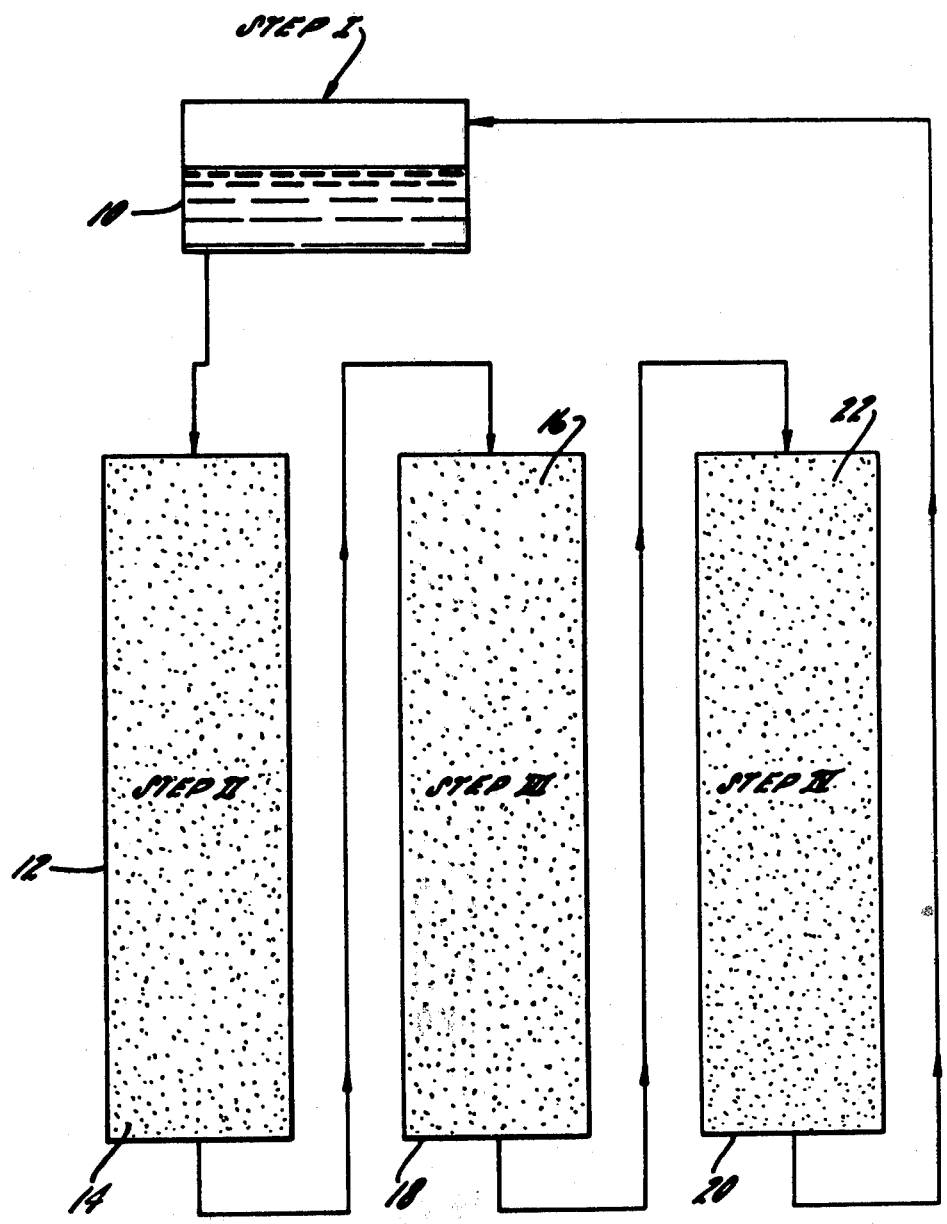

MOLECULAR TRANSFORMATION PROCEDURE

This is a division, of application Ser. No. 907,503, filed May 19, 1978 U.S. Pat. No. 4,182,654, issued Jan. 8, 1980, and a continuation-in-part of Ser. No. 680,462, filed Apr. 26, 1976 now abandoned, which application in turn is a continuation-in-part of Ser. No. 507,198, filed Sept. 18, 1974 now abandoned.

The present invention relates to molecular transformation procedures useful in the synthetic preparation of organic and biochemical materials and, more particularly, to the preparation of biologically active polymers such as peptides and the like.

The area of peptide synthesis has received considerable attention in recent years. A significant problem has existed in synthetically achieving a high molecular weight, pure polypeptide wherein the amino acid sequence of the peptide actually prepared corresponds to that sought. To approach realization of the synthesis with the desired purity has heretofore been quite laborious.

The synthetic preparation of a polypeptide is a multi-stage molecular transformation procedure whereby a desired product is constructed by sequential chemical reactions of a precursor and an added compound, with the precursor at any given stage being the chemically reacted, reactable precursor from the preceding stage. Thus, the procedure is reiterative.

In this process a first amino acid is reacted with a second to form a dipeptide, schematically represented by formula I

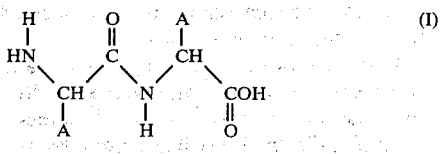

The peptide so formed at this stage is separated from the unreacted acids and a third amino acid is then reacted with the dipeptide to form a tripeptide. The procedure is reiterated until a polypeptide having the desired amino acid sequence, customarily termed the target peptide, is obtained. Sequence failure, whereby a portion of the elongated polypeptide chains have an improper amino acid sequence, can result from several causes. One can be the failure to remove residual free acid from the reaction mixture prior to reaction with a subsequent amino acid. The presence of such unreacted acid presents the possibility that a portion of the chains will be improperly elongated with the residual acid rather than with the acid desired at that stage of the sequence.

Yet a further and perhaps more significant cause of sequence failure is the incomplete reaction of all of the chains present with the amino acid added at each stage of the synthesis. In the preparation of low molecular weight polypeptides, the presence of chains containing different numbers of acids can be analytically ascertained and the desired peptide chains isolated. Conventional analytical techniques do not permit this to be done with respect to the higher molecular weight varieties, however, because the difference in molecular weight between properly and improperly synthesized chains is simply too small to be detectable.

The peptide synthesis procedure described above has been represented as involving the sequential reaction of amino acids with a polypeptide chain. In this respect, there are two approaches; one being growth of the peptide from the C-terminal end (the end of the chain with the

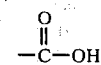

group) and the other being growth from the N-terminal end (the end with the —NH$_2$ group). It is well recognized that during the synthesis either the alpha amino group (N-terminal route) or carboxyl group (C-terminal route) of the added acid must be blocked so that the added acid reacts with the polypeptide chain and reaction between the molecules of added acid cannot occur. It is necessary, therefore, that the blocked group of the added acid, after reaction with the chain, be deblocked for the subsequent acid addition step. Failure to achieve deblocking at any stage of the synthesis can introduce a sequence failure. Moreover, deblocking must be accomplished in a fashion whereby the peptide being synthesized is not adversely affected.

In order to achieve solubility, conventional methods of peptide synthesis customarily are carried out in a non-aqueous medium, particularly for high molecular weight peptides containing protected amino acid side chains. This has necessitated the use of harsh coupling reactions to effect peptide bond formation and the accompanying likelihood of chain disruption such as racemization or fragmentation. Moreover, especially with respect to the higher molecular weight polypeptides, non-aqueous reaction solutions may not permit the peptide to assume its naturally occurring configuration. In nature, of course, the peptides are manufactured in an aqueous environment.

Accordingly, the present invention provides an improved method for preparing a substantially pure polypeptide of predictable amino acid sequence, which method is susceptible to automation and which can reliably be used to prepare pure, high molecular weight target peptides.

The present invention also provides a method for isolating an elongated polypeptide from its reaction environment so that the proper sequence can result on further reaction, which method is easy to accomplish with a minimum expenditure of time and minimum peptide loss.

The present invention further provides a facile method for minimizing the difficulties attendant on the reiterative preparation of polymers which result from sequence failure due to incomplete reaction by efficiently removing failed sequences from the growing chain population so that recovery of a desired pure polypeptide can be accomplished more conveniently.

This invention further provides a novel method for deblocking a peptide which is easy to accomplish and does not result in destruction of the chain being fashioned. In addition, the deblocking is accomplished in a manner which ensures the optical purity of the peptide being formed.

The present invention further provides a method for peptide synthesis wherein the reiterative elongation of the growing chain can be rapidly accomplished in an aqueous medium without disruption of the polymer chain. Additionally, the present invention provides a peptide synthesis procedure which does not necessitate elaborate protection of amino acid side chains which customarily decrease the aqueous solubility of the polymer being prepared.

The present invention provides a process for synthesizing a peptide chain having a distinct sequence of amino acid segments which comprises (1) reacting a pure precursor complex, wherein a first amino acid segment of the peptide chain to be prepared is covalently bonded to a handle, and wherein said segment contains a free terminal carboxyl group or a free terminal amino group, with a second amino acid segment containing a free $N^\alpha$-amino group and a blocked carboxyl group when the precursor has a free terminal carboxyl group or a free carboxyl group and a blocked $N^\alpha$-amino group when the precursor has a free terminal amino group, in an aqueous medium;

(2) optionally removing the unreacted precursor complex;

(3) reversibly coupling the handle of the reacted complex to an adsorbent immobilized on an insoluble support;

(4) separating the reacted complex from unreacted second amino acid segment;

(5) releasing the handle from the adsorbent;

(6) optionally deblocking the carboxyl group or amino group on the reacted complex;

(7) optionally reiterating steps (1) to (6) until the desired number of amino acid segments are added to the precursor;

(8) optionally releasing the peptide chain from the handle and recovering the product.

The present invention also provides a process for synthesizing a peptide chain having a distinct sequence of amino acid segments which comprises reacting a pure precursor containing a first amino acid segment of the peptide chain to be prepared having a free terminal carboxyl group or a free terminal amino group, with a second amino acid segment containing a free $N^\alpha$-amino group and a blocked carboxyl group susceptible to enzymatic hydrolysis when the precursor has a free terminal carboxyl group or a free carboxyl group and a blocked $N^\alpha$-amino group susceptible to enzymatic hydrolysis when the precursor has a free terminal amino group, in an aqueous medium; and deblocking the product peptide enzymatically.

The present invention further provides a process for preparing a peptide chain having a distinct sequence of amino acid segments which comprises reacting a pure precursor containing a first amino acid segment of the peptide chain to be prepared having a free terminal carboxyl group or a free terminal amino group, with a second amino acid segment containing a free $N^\alpha$-amino group and a blocked carboxyl group when the precursor has a free terminal carboxyl group or a free carboxyl group and a blocked $N^\alpha$-amino group when the precursor has a free terminal amino group, in an aqueous medium; and removing unreacted precursor by enzymatic degradation or by scavenging.

According to the present process, chain elongation in solution can be accomplished by reacting a precursor complex with the selected sequencing segment to be added at a particular stage of the polymer synthesis. The precursor complex can, of course, contain the initial segment of the chain or an existing chain of segments onto which additional segments are to be attached. For the purposes of this invention, the use of the term "segment" or "amino acid segment" includes, where applicable, derivatives of the segment which actually exist in the ultimate chain being fashioned. The term "segment" or "amino acid segment" can refer to a single amino acid or a series of amino acids.

In polypeptide synthesis the added segment is an amino acid residue and the precursor is an elongatable peptide chain having either a free terminal amino or carboxyl group. Peptide bond formation and chain elongation thus is accomplished through either acylation of the amino group on the chain by the carboxyl moiety of the acid being added (N-terminal route) or acylation of the amino group of the added acid by the carboxyl group on the growing chain (C-terminal route).

Preferably, the precursor is part of a larger, water soluble complex which contains a water soluble handle attached to the precursor through the non-elongatable end thereof. That is, for C-terminal chain growth the chain is anchored to the handle at the $N^\alpha$-group of the first amino acid residue of the sequence. For N-terminal growth the chain is anchored to the handle through the carboxyl group of the first amino acid residue of the sequence. Chain elongation, therefore, is effected while the precursor is a part of the complex. So that the complex is stable in aqueous medium, attachment between the handle and precursor is preferably covalent and effected in a manner which pemits subsequent release so that eventual recovery of synthesized, pure target fragment can be effected. Since the growing chain is covalently complexed to the water soluble handle, aqueous solubility of the chain during the addition reaction is markedly enhanced, even when the chain is quite large. Also, as later described, the use of a handle such as a polynucleotide, can facilitate separation of the complex from its reaction environment.

Water soluble synthetic polymers are a class of substances which can be employed as handles. Representative examples of this class of substances are polyvinyl alcohol, polyvinylpyrrolidone, poly(acrylamide-acrylic acid) or polyethylenemaleic anhydride. Polyamides such as those amino acid polymers containing a glutamic acid or aspartic acid segment also are suitable substances for use as handles. Another useful substance which can be used as a handle is polyethyleneglycol.

Water soluble polynucleotides also constitute a useful class of substances which can be employed as handles. Representative examples of useful polynucleotides, named as acids, include polyadenylic acid, polyuridylic acid, polythymidylic acid, polycytidylic acid and polyguanylic acid. Preferably the acids have at least ten repeating ribosephosphate moieties and are commercially available.

The manner of achieving attachment of the first amino acid, or a short chain peptide, to a handle should be such that the target peptide can be thereafter removed under mild conditions. To this end, a further aspect of the present invention resides in including, as a part of the handle, an endopeptidase-specific spacer arm onto which the first protected amino acid segment of the target peptide is added. The configuration of this spacer varies with respect to the synthetic route, that is C- or N-terminal, to be employed. The use of an endopeptidase specific spacer arm has the advantage of mild pH and temperature conditions for removal of the target peptide. While, for example, saponification can be used in an N-terminal route if the first amino acid of the peptide is attached directly to a polynucleotide handle, saponification is harsh and can lead to racemization.

Thus, considering attachment in more detail, for synthesis via the C-terminal route with a polynucleotide containing handle, the ribose of the 3' end of a polynucleotide is oxidized to a dialdehyde with subsequent coupling to an endopeptidase specific spacer arm by reductive alkylation which involves formation of an amine, dialdehyde adduct followed by reduction of that adduct in aqueous solution with, for example, sodium borohydride. Therefore, the arm has, on one end, a primary amino group reactable with the oxidized ribose moiety of the nucleotide. The other end thereof contains a carboxyl group which, after having acylated a $N^\alpha$-amino group of an added acid, can be hydrolyzed by the action of an endopeptidase. Polypeptides themselves containing a carboxyl terminated arginine or lysine residue constitute a useful class of such spacers, especially where the N-terminal residue, or other residues, are from hydrophobic acids requiring no protection such as glycine, alanine, or valine. The dipeptide, glycyl-L-arginine, is a useful spacer arm which can be coupled, by reductive alkylation, to a polynucleotide according to the method of Royer, et al., BBRC, 64, 478 (1975). The dipeptide spacer, attached via a tertiary amine linkage to the nucleotide, thus has a free carboxyl group available for addition of a first carboxyl protected amino acid or polyacid segment for the preparation of a target peptide by the C-terminal route.

When the use of polyethyleneglycol or polyvinyl alcohol as a handle is desired, the alcohol group is converted to an alkoxide derivative, for example by reaction with potassium tert-butoxide, and the alkoxide derivative is reacted with ethyl bromoacetate to provide the carboxymethyl derivative. This derivative is hydrolyzed to give the free acid which is coupled to the endopeptidase specific spacer arm using a water soluble carbodiimide activator.

Polyvinylpyrrolidone, poly(acrylamide-acrylic acid) and polyethylenemaleic anhydride are subjected to basic hydrolysis to form derivatives having free carboxyl groups. The polyamides are selected from those having a free carboxyl group. These substances also are coupled with the spacer arm as stated above.

After preparation, removal of the target peptide from its complex with the handle can be effected by use of a highly specific endopeptidase, for example, trypsin, which cleaves only those peptide bonds whose carbonyl is that of arginine (or lysine). The enzyme for this cleavage can be used either bound to a support or free in solution at mild alkaline pH.

For N-terminal peptide synthesis, preparation of the polynucleotide handle again requires oxidation of the ribose moiety, with a spacer arm being attached thereto through a secondary amine linkage via reductive alkylation. However, in this case, the end of the spacer arm disposed for covalent coupling to the first amino acid to be added must contain a free amino group so that N-terminal chain growth can occur. Thus, the spacer arm contains a primary amine group in both terminal positions, one to react with the nucleotide and the other to complex with the first acid residue of the sequence. Moreover, in order to also have the required endopeptidase activity necessary for eventual removal of the target peptide from the handle, the amine group used for covalent coupling to the first acid residue of the desired sequence can be provided by the alpha-amino group of arginine or lysine or derivatives thereof.

One convenient manner of preparing the handle for N-terminal chain growth is to first reductively couple a short chain diamine to the aldehyde containing nucleotide, Royer et al., supra. Thereafter, $N^\alpha$-amino protected arginine or lysine, eg, PC-L-ArgOH, is attached through the acid carboxyl group to the available amine of the diamine, for example by using a water soluble carbodiimide activator, and the protecting group removed, for example by using the enzyme L-pyrrolidone-carboxylpeptidase, to yield the desired handle having a free amino group available for peptide synthesis by the N-terminal route.

When use of a vinyl polymer or polyamide handle is desired, derivatives containing a free carboxyl group are prepared as above. The carboxyl derivative is coupled with a diamine, such as ethylenediamine, using a carbodiimide. The $N^\alpha$-amino protected arginine or lysine spacer arm is attached to the diamine as indicated above for polynucleotide handles.

Subsequent recovery of the target peptide from the handle can be effected by the two stage use of an arginine or lysine specific endopeptidase as previously discussed followed by an arginine or lysine specific exopeptidase, for example carboxypeptidase B. The first enzyme releases the arginine or lysine terminating target peptide from the remainder of the handle while the second removes the C-terminal arginine or lysine residue and simultaneously liberates the target peptide. As stated above, both enzymes may be used bound or in solution at mild alkaline pH.

If lysine or arginine is to be present in the target peptide, the side chains of these amino acid segments must be protected. If such side chains are not protected, the target peptide itself would be fragmented by the endopeptidase used for separation from the handle. Typical protecting groups are trifluoroacetyl for the epsilon amino group of lysine and nitro group protection for the guanidinium side chain of arginine. Deprotection of these residues can be accomplished by routine procedures well known for this purpose after separation of the target peptide from the handle.

In building a spacer arm having arginine as the terminal acid for reaction with the first amino acid of the target peptide, it has been found that enhanced coupling yield is obtained if nitro protected arginine is used. To achieve subsequent enzymatic release of the target peptide at the arginine linkage, the nitro protecting group must first be removed. Where the target peptide itself contains arginine, added in protected form as above described, deprotection of arginine in the handle is accomplished before addition of further arginine, eg, after several non-arginine amino acid residues have been added.

A further useful type of spacer arm is one which can be chemically released from the target peptide under mild conditions. Cyanogen bromide cleavage at the carboxyl end of methionine (Met) is an embodiment of this aspect, eg, with about a 100 fold excess of CnBr, cleavage is achieved in water in about 1 hour at 30° C. Thus, a spacer arm joined to the target peptide through the Met carboxyl group is useful for C-terminal peptide growth. For N-terminal growth, Met in the spacer arm is separated from the first amino acid of the target peptide by a basic amino acid such as arginine. Met cleavage with cyanogen bromide then yields the target peptide with the Arg-homoserine lactone dipeptide terminus. The lactone is first removed with the enzyme CPA followed by removal of Arg with CPB to yield the target peptide. Again, if Met occurs in the sequence of the target peptide, protection, eg, formation of the sulfoxide, is necessary. After release from the handle, methionine sulfoxide is reduced to methionine with a thiol such as mercapto ethanol.

In order to prevent the added amino acid from reacting with itself during chain elongation, the primary alpha amino group or, as the case may be, the carboxyl group thereof, as well as other reactive groups except for the intended reactive moiety, must be appropriately blocked or protected. As hereinafter discussed, a preferred blocking or protecting group for an alpha amino group or carboxyl group is one which can be enzymatically removed. Hereinafter, the symbol, $\alpha$, refers to the term alpha.

A preferred aspect of the present invention, particularly with respect to peptide synthesis by the C-terminal route, resides in using non-activated amino acid ester derivatives containing a free $N^\alpha$-amino group to effect reaction with the precursor. Compounds within this class include those prepared from single amino acids as well as other compounds such as, for example, those containing one or more peptide bonds prepared from the same or different amino acids. These amino acid derivatives containing an ester blocked carboxyl group can be represented as follows:

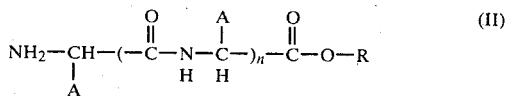
(II)

wherein n is an integer of zero or more; A is an amino acid side chain which can be different in each repeating unit when n is greater than zero; and R is a blocking group which prevents the derivative from acylating a molecule containing a free amino group. Preferably, R is a short chain, less than about 10 carbon atoms, straight or branched alkyl group, which as hereinafter discussed can be removed enzymatically. Other suitable ester groups are the benzyl and nitrobenzyl groups.

The derivatives represented by formula II above are prepared by known esterification techniques such as the acid-catalyzed reaction of an amino acid with an alcohol. Using these derivatives, reaction with a precursor containing a free carboxyl group can be accomplished at ambient temperature in water at acid pH utilizing a water soluble carbodiimide as a coupling reagent. Because of coupling at an acid pH value, racemization is minimized.

When an N-terminal route is selected, again the conventional means of coupling an $N^\alpha$-blocked acid to the free amino precursor involving use of a water soluble carbodiimide is an attractive and practical approach. Preferably, as will be discussed, the $N^\alpha$-blocking group is enzymatically removable. Another coupling means is the use of active $N^\alpha$-blocked amino acid derivatives to effect reaction with the precursor. Active amino acid esters are one example of such derivatives. As is recognized (Bodanszky and Klausner, *The Chemistry of Polypeptides*, ed. Katsoyannis, p. 21, Plenum, 1973), these active esters spontaneously form peptide bonds in solution at room temperature with minimal adverse racemization.

The active esters can be prepared by reacting the acid moiety of a $N^\alpha$-protected amino acid with an alcohol having substituents which make it readily displaceable by an attacking amino group on the precursor chain. The preparatory reaction can be accomplished in an organic solvent in the presence of a carbodiimide. Aliphatic alcohols containing one or more electron withdrawing groups, phenol (and thiophenol) derivatives and hydroxylamine derivatives are useful alcohols. Particular examples of useful active esters are those containing the following displaceable leaving groups: cyanomethyl, carboethoxymethyl, propargyl, N-hydroxysuccinimide, N-hydroxylphthalimide, p-nitrophenyl, 2,4,5-trichlorophenyl, as well as others given in the foregoing reference. While the active esters are preferred, amino acid derivatives prepared with other readily displaceable groups on the carboxyl moiety are also useful. These groups include, for example, those such as azido, imidazole, halo, acyl and phosphoryl.

With enzymatically deblockable $N^\alpha$-groups, the active amino acid derivatives, and especially the esters, constitute a useful class of compounds for peptide synthesis using the N-terminal route. Both the acylation reaction with the chain and the deblocking procedure for subsequent elongation can be accomplished in solution under very mild conditions, thus minimizing any adverse effects on the polymer being synthesized. Also, as will be hereinafter discussed, the use of the active esters can obviate blocking other side chains on certain amino acids which ordinarily need appropriate protection.

In essential aspects, the compounds constituting the above class of active esters are those which contain an amino acid derivative having an activated terminal carboxyl group and an N-blocking group susceptible to removal by a corresponding and specific enzyme. In one embodiment, these compounds can be represented as follows:

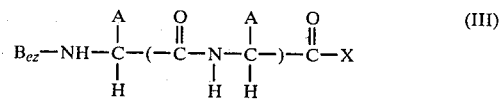
(III)

wherein $B_{ez}$ is an enzymatically removable $N^\alpha$-blocking group; X is a group readily displaceable by an amino group; and n and A are as identified with respect to formula II. The L-pyrrolidonecarboxyl (pyroglutamyl) group is a useful $N^\alpha$-acyl blocking group. Kurath and Thomas, *Helv. Chim. Acta*, 56, 1658 (1973) and Doolittle, *Methods in Enzymol*, 19, 558 (1970) illustrate the manner in which L-pyrrolidonecarboxylic acid can be used to prepare the $N^\alpha$-L-pyrrolidonecarboxyl derivatives of amino acids.

The first of these methods involves preparing a N-protected pyrrolidonecarboxyl N-hydroxysuccinimide ester (Z-PC-NHS) by the dicyclohexyl carbodiimide mediated coupling of benzyloxycarbonyl (Z) protected pyrrolidone carboxylic acid (PC) to N-hydroxysuccinimide (NHS). The resulting Z-PC-NHS dissolved in a solvent is then coupled in aqueous solution in the presence of a base with an amino acid (AAOH) to form the Z-PC protected acid (Z-PC-AA-OH). Removal of the Z group is then accomplished by catalytic hydrogenation yielding the pyrrolidonecarboxyl protected amino acid. Alternatively, a trifluoroacetyl protecting group can be used in place of Z which can be removed by a pH adjustment to 10.

The Doolittle method involves reaction of the t-butyl amino acid esters with PC in the presence of a carbodiimide in an organic solvent followed by removal of the butyl group and acid regeneration. However, low yields are likely.

To obtain high conversion, the elongation reaction can be accomplished with a large excess of the added sequencing segment, amounting to at least a 2:1 equivalent ratio, and preferably at least 5:1. However, the solution after reaction may nevertheless contain unreacted transformable precursor. In a reiterative procedure, the presence of such unreacted precursor can produce a sequence failure. While blocking of the unreacted precursor could be accomplished prior to the next reaction, blocking does not alter the molecular structure of the precursor and the possibility of sequence failure continues to exist if deblocking was to occur subsequently.

Therefore, a further aspect of this invention centers on pruning. Pruning is selectively and chemically removing unreacted precursor from reacted compound after the formation of the latter, thereby leaving a properly reacted compound which is free of material containing the base molecular structure of the unreacted precursor. Pruning is important in achieving ultimate separation and recovery of a pure target peptide.

With particular respect to the synthesis of polypeptides, which are elongated through acylation of a terminal amino on the precursor using $N^\alpha$-blocked, free carboxyl segments or through acylation of a free $N^\alpha$-amino group on a C-terminal carboxyl blocked segment by a free carboxyl group on the precursor, pruning can be effected by enzymatically hydrolyzing those precursor chains which failed to elongate and thereby degrading such chains. The unreacted chains, of course, still contain either a free amino group in the case of N-terminal growth, or a carboxyl group in the C-terminal case, and thus can be enzymatically attacked using an appropriate enzyme. On the other hand, those chains which did properly elongate will have their terminal reactive group (either amino or carboxyl) protected by a blocking group and will not undergo hydrolysis.

A preferred method of enzymatic pruning is to pass the reaction solution through a column which contains a water insoluble support material having immobilized on its surface an enzyme which selectively hydrolyzes substances either from the N-terminus or C-terminus. An aminopeptidase, such as aminopeptidase M or leucine aminopeptidase, is suitable for hydrolysis at the N-terminus (Royer and Andrews, 1973, *J. Biol. Chem*, 248, 1807). The hydrolysis is carried out at a temperature between 0° and 50° C. and at a pH of 6.5 to 7.5. For hydrolysis directed at the C-terminus, a carboxypeptidase such as carboxypeptidase A, B, C or Y is useful. These Y and C enzymes, at pH 4–6, have been demonstrated as having non-specific, C-terminal exopeptidase activity. Hayashi et al., *J. Biol. Chem.*, 248, 2296 (1973) and Kuhn et al., *Biochemistry*, 13, 3871 (1974). A temperature between 0° and 60° C. is employed. All of these enzymes are specific for L-amino acid residues and, as will be hereinafter discussed, unreacted precursor will only be present in the L-isomer form.

An alternative method of pruning involves scavenging the unreacted precursor from the reaction solution, such as by attaching it to a water insoluble support, and thereafter separating the solution from the support. With particular respect to a precursor having a free amino terminus, a manner of accomplishing this is to immobilize onto a support an electrophilic reagent which has specific covalent reactivity for the free terminal amino group of the unreacted precursor and, thereafter, pass the reaction solution into intimate contact with the support in order to bond the unreacted precursor thereto. A suitable electrophilic reagent is the mixed disulfide formed by reaction of a thiol derivative and mercaptosuccinic anhydride. For C-terminal scavenging, a support containing free primary amino groups can be used in conjunction with water soluble carbodiimides.

Subsequent to pruning of unreacted precursor, the properly elongated chains are separated and recovered from excess unreacted amino acid. This separation preferably is effected while the elongated complex is reversibly coupled to an insoluble support. Reversible coupling, for the instant purposes, is to be considered as attachment by means of a non-covalent and non-ionic association between two substances which have a specific affinity for each other in an aqueous medium, which affinity can be dissipated without chemical reaction. Reversible coupling thus permits attachment to and release from the support without the use of harsh conditions which might adversely affect the transformed compound.

To achieve reversible coupling to the support, the precursor can be one part of a larger, water soluble complex which contains a polynucleotide handle attached to the precursor through the non-elongatable end thereof. The insoluble support conveniently is contained in a column and has covalently affixed to its surface a polynucleotide adsorbent which has specific affinity for the polynucleotide handle complexed to the reactor precursor. As the solution containing the complex is passed through the column, the elongated precursor is reversibly coupled to the insoluble support by affinitive interaction between the handle and the adsorbent. Separation of the elongated chains, in complexed form, from chemically unrelated substances, such as the unreacted amino acid reactant which does not contain the covalently bonded handle, is thereby effected. The coupling can be simply reversed by heat, the institution of a competing association, or a change of pH. In order to achieve reversible coupling, the polynucleotide selected as the handle should have a base which is complementary, as to spatial arrangement and affinitive interaction, with the base of the polynucleotide adsorbent. Examples of useful complementary base pairs are adenine with either uracil or thymine and cytosine with guanine. It should be appreciated that polynucleotides of the "copolymer" type also can be used, especially when they are of the "block" form containing alternating and repeating segments of complementary base pairs. In this instance, of course, the same polynucleotide can be used as both the handle and adsorbent.

When the elongation reaction is carried out using a precursor which contains a polyethylene glycol, vinyl polymer or polyamide handle, separation of the unreacted added amine acid segment is carried out by conventional methods, such as dialysis, ultrafiltration, extraction, etc.

A further preferred feature of the present invention provides a method for enzymatically deblocking the elongated complex before it is used as a further precursor in subsequent stages. Here it is, of course, necessary that the blocking group on the elongated complex be selectively degradable by enzymatic action.

Turning first to that aspect of the present invention wherein chain elongation is accomplished through the C-terminal end of a growing chain by reaction with an amino acid segment of Formula II, the blocking group on the acid segment is a short chain alkyl group or benzyl group coupled to the acid through an ester linkage. One reason for this is that deblocking after reaction with the precursor can be accomplished enzymatically using an esterase, thereby hydrolyzing off the ester group to yield the free C-terminal carboxyl group for subsequent elongation of the chain. A carboxypeptidase such as carboxypeptidase Y is useful for this purpose so long as the pH is maintained in the range of pH 8–9, preferably at pH 8.5. At a pH of 8.5 this enzyme exhibits optimum esterase activity to the exclusion of peptidase activity, while, as previously discussed, at a lower pH it is exclusively an exopeptidase. The hydrolysis reaction is carried out at a temperature between 0° and 60° C.

A further significant advantage accompanying the use of this enzyme for deblocking is that hydrolysis is only effected with respect to esters of L-amino acids. Thus, those chains containing blocked esters of D-amino acids are not hydrolyzed by the enzyme and are not available for subsequent growth. As a result, a high degree of optical purity with respect to the target peptide can be achieved.

When growth from the N-terminus is desired, the L-pyrrolidonecarboxy group is a useful blocking agent for the α-amino group on the added acid. The elongated complex containing this blocking group then is exposed to an enzyme, such as L-pyrrolidonecarboxylpeptidase, which has the necessary specificity at a temperature between 0° and 60° C. and a pH of 7 to 8. This enzyme is effective in deblocking only derivatives of L-amino acids. Thus, any D-isomer terminating chains remain blocked and are effectively no longer available for subsequent growth.

In either of the foregoing cases, intimate contact should be achieved between the blocking group on the chains and the enzyme in order to effect substantially complete deblocking of the L-terminated chains. Accordingly, it is preferred that contact be achieved while the elongated precursor is dissolved in an aqueous medium. Moreover, in order to easily separate the deblocked compound and the enzyme, and to minimize enzyme loss, the enzyme preferably is immobilized on a water insoluble support. Therefore, a preferred manner of accomplishing the deblocking is to pass the aqueous solution of the blocked elongated complex through a column which contains an insoluble support having the enzyme immobilized thereon. As should be apparent, with respect to C-terminal synthesis, a column containing carboxypeptidase Y immobilized on a water insoluble support may be used both for pruning unreacted precursor and for deblocking the terminal carboxyl group of the blocked elongated complex merely by adjusting the pH to achieve the desired exopeptidase or esterase activity respectively.

Turning now to the combined use of the above features in a multi-stage polypeptide synthesis and with reference to the drawing, the initial step is the reaction in the vessel 10 of a first amino acid derivative with a handle to form a water soluble covalent complex containing the first amino acid residue of the intended sequence. The added acid contains an enzymatically removable $N^\alpha$-amino or C-carboxy protecting group depending on the route selected. Unreacted amino acid derivative is removed from the reaction solution containing the initial complex by passing the solution through a column 18 containing a water insoluble support 16 which has immobilized on its surface an adsorbent which can affinitively interact with the handle. Preferably, when the handle and adsorbent are polynucleotides, the solution is maintained at about 4° C. The support is then washed several times with 7.5 pH phosphate buffer at this temperature. Thereafter, the complex is eluted from the support as an aqueous solution free of the added acid derivative by simply drawing buffer through the column at an elevated temperature, preferably from 40° C.–60° C.

The solution so obtained then is passed through another column 20 in order to remove the blocking group on the terminal acid segment of the complex. Accordingly, this column contains an insoluble support 22 having immobilized on its surface an enzyme having specificity for the protecting group. Then the solution is introduced back into a clean reaction vessel and, since the blocking group has been removed, chain elongation can be effected with the second amino acid of the intended sequence. As with the first acid, the second acid is derivatized so as to be appropriately $N^\alpha$ or C-blocked.

The foregoing procedure (involving steps I, III and IV) is then reiterated to successively add the desired acids on to the complex containing the growing polypeptide chain until a short polypeptide, for example a hexapeptide, has been prepared. It will be noted that, up to this point, pruning of chains which failed to react with added acid has not been employed. As will become apparent, there is no particular advantage to be derived from including this step (Step II) in the early stages of the synthesis, although it can be used without any adverse consequences if desired.

At this point, the solution recovered after separation of unreacted acid from the short chain peptide is enzymatically treated to release the elongated chains from the handle. The solution is passed back over the support containing the immobilized adsorbent to remove the separated handle and the terminal amino or carboxyl blocked short chain target peptide then is isolated from the solution. Since the occurrence of sequence failure in any of the foregoing steps results in the presence of chains having less than, for example, six amino acid residues, separation and isolation of the desired short chain peptide easily can be accomplished by conventional techniques, such as ion exchange or gel filtration chromatography.

The preparation of long chain polypeptides by the process of the present invention may utilize a short chain polypeptide as a precursor. The short chain polypeptide precursor may be prepared by the present process as illustrated above or synthetically prepared by other methods. In addition, naturally occuring short chain polypeptides may be used as the precursor. In any event, the pure short chain polypeptide is attached to the handle, enzymatic deblocking is effected, and the short chain peptide complex then is used as the precursor for chain elongation with the next amino acid derivative. It is at this point that the above described pruning of unreacted chains preferably is initiated (Step II). To this end, the Step I reaction solution, which contains the complex of the elongated polypeptide, unreacted excess blocked acid, and unreacted complex of the short chain polypeptide precursor from the vessel 10 is passed through another column 12 containing an insoluble support 14 having an alpha-amino group or terminal carboxyl-specific exopeptidase immobilized on its surface.

On passing through this column, the unreacted precursor chains, which contain an unblocked terminal amino or carboxyl group, are enzymatically degraded and, therefore, pruned from the desired chain population. Thereafter, this step (Step II) is incorporated into the above described reiterative sequencing procedure as the chain is elongated with additional amino acid derivatives.

Finally, after the desired target polypeptide has been prepared, the polypeptide chains are released from the handle and the target peptide separated and purified. It will be appreciated that, due to the incorporation of the enzymatic degradation step (Step II) for each sequence after the preparation of the short chain polypeptide precursor, the final reaction solution contains very few and, preferably, substantially no polypeptide chains which differ from the target peptide by less than the number of amino acid residues in the precursor. Thus, conventional separation techniques can be used.

Furthermore, it will be appreciated that the foregoing, generally described reiterative procedure, is useful with respect to both the C-terminus and N-terminus routes to peptide synthesis. The principal differences between the two routes reside in the manner in which the growing chain is attached to the handle and in the selection of blocking groups and enzymes. Also, there can be a difference in the manner in which activation for chain elongation is accomplished, for example the use of active esters for N-terminal growth versus carbodiimide mediated coupling. The latter, which is useful with respect to both C- and N-terminal growth, is preferred. Most preferred is the C-terminal approach to chain elongation.

In light of the foregoing discussion, it will be appreciated that the difficulties associated with a sequence failure at any stage can be substantially eliminated so long as (1) a pure transformable precursor is used for reaction at some intermediate stage of the procedure and (2) degradation of unreacted precursor is utilized in all stages subsequent thereto. The minimum point at which the use of a pure polypeptide precursor is necessary depends on the ultimate molecular weight of the polypeptide to be fashioned. The molecular weight of the pure polypeptide precursor can be considered as the minimum molecular weight difference which will exist in the final polymer solution between the desired polypeptide and impure polymer chains. Therefore, as the desired polypeptide increases in molecular weight, the minimum difference between the weight of the pure and impure chains becomes similar for any given pure polypeptide precursor, and the difficulty in eventual purification increases.

Accordingly, while a pure hexapeptide precursor is suitable for the ultimate preparation of a polypeptide containing twenty to about thirty-five amino acid residues, it is to be understood that correspondingly larger pure polypeptide precursors should be used initially for the preparation of higher molecular weight, pure polymers.

Thus, it is apparent that the illustrated procedure itself can be used to prepare pure, high molecular weight precursors for subsequent use in the preparation of even higher molecular weight compounds. For example, a polypeptide containing 35 acid residues prepared as described above can itself be used as the pure precursor for the preparation of a polymer containing upwards of 100 amino acid residues.

The process of the present invention has application in the synthesis of important peptides as glucagon, enkephalin, ACTH, calcitonin, vasopresin, pentagastrin, endorphin, somatastatin, and many others including potentially very large peptides such as insulin and pro-insulin.

As indicated previously, reactive groups other than the alpha amino or carboxyl group on some amino acids must be blocked or protected during chain elongation. As is well recognized, these groups are the epsilon amino group of lysine, the imidazole group of histidine, the phenolic hydroxyl group of tyrosine, the carboxyl groups of glutamic and aspartic acids, the thiol group of cysteine, and the guanidinium group of arginine. Typically, removal of these blocking groups is the final step of the complete synthesis procedure. The following table sets forth examples of recognized protecting groups; see also, *Solid Phase Peptide Synthesis*, Stewart and Young, Freeman and Co., 1969, pp. 13–23, for blocking groups as well as the conditions under which they can be removed.

TABLE

| Acid | Blocking Group | Removal |
|---|---|---|
| Lysine | acetamido or trifluoroacetyl | pH 9, 1.2M hydrazine or 1M piperidine at 0° C. |
| Histidine | ethoxyformyl | pH 9, 1.2M hydrazine |
| Tyrosine | acetyl | pH 9, 1.2M hydrazine |
| Cysteine | acetamidomethyl (Veber et al., 1972, J. Am. Chem. Soc., 94, 5456) | mercuric acetate and then $H_2S$ (to be removed last) |
| Arginine | nitro | catalytic hydrogenolysis |

A particular aspect of the present invention resides in the fact that only certain minimal protection of side groups is necessary. This fact, in combination with the use of a high molecular weight water-soluble handle, is advantageous in achieving water solubility of the growing polypeptide.

Thus, when the above described active esters of amino acids are utilized for chain elongation (N-terminal growth), only the epsilon amino group of lysine and the thiol group of cysteine need be blocked. This results in advantages accompanying initial amino acid preparation as well as avoiding the necessity for eventual deblocking and potential adverse effect on the prepared polypeptide. For C-terminal growth, the carboxylate side groups of glutamic and aspartic acid need to be protected. Also, in view of the procedure discussed above for separating the peptide from the handle, in both routes the $\epsilon$-amino group of lysine and the guanidinium group of arginine also require protection where either of these acids are included in both the handle and the target peptide.

It has been indicated that a water insoluble support for the immobilized adsorbent and enzymes can be employed. While a variety of known water insoluble materials either organic or inorganic, can be used so long as they do not adversely affect the growing polymer chain or complex thereof, the support preferably is rigid and dimensionally stable in changing solution so that it can tolerate various reaction conditions. Porous glass beads constitute an especially preferred class of rigid supports. As hereinafter illustrated, these beads can be suitably derivatized and activated so as to effect immobilization of enzymes and adsorbents thereof. Pierce Chemical Company of Rockford, Illinois, is a commercial source of such beads. A particularly useful support is ∓Glycophase" G porous glass beads. These beads are the 2,3-dihydroxypropyloxypropyltrimethoxy silane derivative of porous glass.

Also, it is to be understood that the aqueous solutions referred to herein can contain organic solvents or other ingredients which do not adversely affect the desirable features of the described procedures. Use of organic solvents such as dimethylformamide or methanol, in fact, are considered to be desirable with respect to the preparation of high molecular weight polypeptides in order to assure solubility. However, the type thereof and amount should be selected so as not to interfere with reversible coupling in the separation step.

The following examples illustrate the manner in which the present invention can be accomplished:

EXAMPLE 1

A. Preparation of Immobilized Enzymes

Five columns are prepared each containing a particular enzyme immobilized on 10 grams of "Glycophase" G porous glass beads (74–126 micron, pore diameter about 550 angstroms) obtained from Pierce Chemical Company or, with respect to carboxypeptidase Y, CL-Sepharose from Pharmacia. Depending on the enzyme used, the glass is activated to facilitate enzyme attachment by one of three approaches. Approach (a) involves adding 10 grams of the beads to a beaker containing water. Ten grams of cyanogen bromide is then added and, while maintaining the solution temperature at 20° C., the pH of the solution is held constant at 11 by the continuous addition of cold 6 N sodium hydroxide. Activation is considered complete, usually in about 15 minutes, when the uptake of the sodium hydroxide ends, such as indicated by a change in pH. At that time, the beads are filtered from the solution and washed with a solution of 0.1 M sodium bicarbonate at a pH of 9.5. Approach (b) involves reacting 10 g. of the beads with 0.5 g. paranitrobenzyl bromide in 50 ml. of dioxane for 24 hours at room temperature, followed by heating at 100° C. in a 10% aqueous solution of dithionite. The arylamine derivatized "Glycophase" G beads are washed with distilled water and are activated by diazotization in 30 ml. of 0.5 N HCL at 0° C. with an excess of NaNO$_2$ followed by washing the activated beads with 3 liters of 3% sulfamic acid and 20 l. of distilled water. Approach (c) involves reaction with NaIO$_4$, Royer et al., supra. The columns and method of enzyme attachment (200 mg. of enzyme used) is given in the following table.

| Column | Enzyme | Activation Approach | Method of Attachment |
|---|---|---|---|
| 1 | L-pyrrolidonecarboxylpeptidase | (a) | 6 hours at pH 8, 4° C. in 0.1M 2-pyrrolidone aqueous medium containing bicarbonate buffer. |
| 2 | Aminopeptidase M | (b) | At pH 7.6 in tris containing MnCl (1mN), Royer et al., J. Bio. Chem., 248 (5), 1807 (1973). |
| 3 | Carboxypeptidase Y | | Conversion of Sepharose to hexamethylene diamine derivative by reductive alkylation followed by enzyme coupling with water soluble carbodiimide at pH 4.75, 12 hours, 0–4° C. |
| 4 | Trypsin | (c) | Reductive alkylation |
| 5 | Carboxypeptidase B | (c) | Reductive alkylation |

B. Preparation of Immobilized Polynucleotide Adsorbent

The arylamine derivative of "Glycophase" G porous glass beads is prepared and activated by approach (b), supra. The beads are reacted at 0° C. for 3 hours with 100 mg. of commercial polyadenylic acid (Poly A) (MW above ∼1000) in buffer at pH 8. After washing, the beads contain about 1%, by weight, of the acid.

EXAMPLE 2

(N-terminal approach)

A. Preparation of active esters of N$^\alpha$-L-Pyrrolidonecarboxyl-L-amino acids Samples of the following L-pyrrolidonecarboxyl blocked amino acids are obtained in substantially pure form by the method of Kurath and Thomas, supra:
L-Alanine;
Glycine;
S-ACM-L-Cysteine;
L-Phenylalanine;
ε-TFA-L-Lysine;
L-Arginine;
L-Leucine;
L-Serine;
L-Tyrosine;
L-Valine.

Thus, 0.1 moles of commercially available protected pyrrolidone carboxylic acid (Z-PC-OH) and 0.11 moles of N-hydroxysuccinimide (NHS) are cooled to 0° in 100 ml. 1,2-dimethoxyethane. Dicyclohexyl carbodiimide (0.11 moles) is added. The reaction mixture is stirred for 2 hours at 0°–40° C. and then overnight at room temperature. The dicyclohexyl urea is removed by filtration and washed with additional 1,2-dimethoxyethane. The filtrates are reduced at 40° C. in vacuo. The N-protected pyrrolidonecarboxyl N-hydroxysuccinimide (Z-PC-NHS) ester is crystallized from 2-propanol. The Z-PC-NHS (6.0 mmoles) is dissolved in 20 ml. dioxane. A solution (10 ml.) containing NaCO$_3$.H$_2$O (7.6 mmoles) and the desired amino acid (7.6 mmoles) is added and the mixture stirred for 4 hours at room temperature. The volume is reduced to 4 ml. After neutralization with 1 N HCl, a precipitate results which is washed with two, 2 ml.-portions of water. The material (Z-PC-Acid) is recrystallized from 2-propanol. Z-PC-Acid (about 1 g.), Pd-back (1 g.) and 200 ml. of 50% aqueous methanol are placed in a 3-necked flask. Hydrogen gas is passed through the suspension for 3 hours at room temperature. After removal of methanol and water, the L-pyrrolidonecarboxyl blocked amino acid is crystallized from methanol-ether.

Having obtained the L-pyrrolidonecarboxyl blocked amino acid by the above method, the N-hydroxysuccinimide active ester thereof is prepared by adding one equivalent of each blocked acid to separate reaction vessels containing ethyl acetate, one equivalent of N-hydroxysuccinimide and 1.1 equivalents of dicyclohexylcarbodiimide. Esterification of the free carboxyl group is effected by stirring for 4 hours at room temperature. The reaction solutions are then removed from the vessels. Precipitated dicyclohexyl urea is filtered off and the active esters purified by recrystallization from ethyl acetate-petroleum ether.

B. Preparation of Polynucleotide-First Acid Complex

Polyuridylic acid (Poly U) (10 mg.) is oxidized with 0.01 M $NaIO_4$ for 18 hours. The resulting aldehyde containing product is reductively alkylated with hexamethylene diamine according to Royer, et al., *Biochem. Biophys. Research Commun.*, 64, 478 (1975). The solution at 4° C., is drawn through the column prepared in Example 1B containing immobilized Poly A which selectively adsorbs the diamine derivatized Poly U. After washing the column and raising its temperature to 55° C., the diamine derivatized Poly U is eluted therefrom in phosphate buffer (pH 7.5). PC-L-arg-OH then is bound to the diamine derivatized Poly U using water-soluble 1-ethyl-3-(3-dimethylaminopropyl)-carbodiimide at pH 4.75 and the PC blocking group then is removed by passing the solution through column 1 prepared as in Example 1A. Subsequently, a large excess of the activated ester of the valine acid prepared as in Example 2A is added to the solution and the solution is stirred for two hours.

C. The Procedure

Two-hundred milliliters of the solution from 2B above, containing the Handle-Arg-Val complex, at 4° C., is passed by suction at 5 ml/minute through the column prepared in Example 1B containing the immobilized polyadenylic acid beads. The column is then washed at 4° C. with 1 liter portions of water at 15 ml/min. to remove unreacted acid. Thereafter the temperature of the column is raised to 55° C. and a 200 ml. portion of phosphate buffer (pH 7.5) at this temperature is drawn through the column at 5 ml/min. to elute the polynucleotide-valine complex.

The solution, at pH 7.5 and 25° C., containing the complex is then passed, at 5 ml/min., through packed column 1 containing the immobilized pyrrolidonecarboxylpeptidase to remove the pyrrolidonecarboxyl blocking group, thus providing 200 ml. of solution which contains the complex of handle, Arg, and valine with a free alpha-amino group.

This solution is then added back into a clean reaction vessel and the foregoing procedure repeated with the sequential addition of samples containing the activated and blocked lysine, phenylalanine, cysteine, and alanine.

After preparation of the hexapeptide solution free of unreacted alanine derivative and before removal of the blocking group, the solution is passed through column 4, containing immobilized trypsin, to release the chains from the handle. Separation of the pure, blocked hexapeptide is then effected by passing the solution over the column containing immobilized polyadenylic acid to remove the handle followed by chromatography.

Subsequently the arginine carboxyl group of the hexapeptide is NHS activated by esterification and recomplexed to the handle as in 2A and B above, deblocked (column 1) and reacted with the sample of glycine prepared as in 2A. Passage of the resulting solution, at 5 ml/min., is then effected, at 35° C., through the column containing immobilized aminopeptidase M (column 2) to degrade any of the hexapeptide chains which failed to react with glycine. This step is thereafter incorporated into the synthesis procedure for the addition of leucine, tyrosine and serine acids.

After the serine acid has been affixed to the growing chain and the complex separated from the reaction mixture, the solution containing the complex is passed through column 4 to remove the handle and treated with 1 M piperidine at 0° C. for one hour to remove the trifluoroacetyl blocking group on the lysine residue. The resulting solution is then passed at 5 ml/min. through the packed column of immobilized pyrrolidonecarboxylpeptidase (column 1) to remove the terminal pyrrolidonecarboxyl group on the serine acid residue and the solution then treated at pH 4 with mercuric acetate and stirred for one hour at 25° C. to remove the acetamidomethyl protecting group on the cysteine residue. The resulting thio compound is generated by bubbling $H_2S$ through the solution. Finally, the pure decapeptide, Arg-Val-Lys-Phe-Lys-Ala-Gly-Lue-Tyr-Ser, is separated and isolated from residual Poly U and other ingredients as illustrated above.

The foregoing example has illustrated the preparation of a polypeptide with an arginine carboxyl terminus and, accordingly, arginine was considered to be a part of the target peptide rather than a part of the spacer arm of the handle. If, for example, the target peptide was the nonapeptide terminating with valine, the synthesis would be the same except that Arg would have been considered to be a part of the handle. After cleavage with trypsin at the carboxyl group, the target peptide with Arg attached would be passed through column 5 containing carboxypeptidase B to remove Arg and release the target nonapeptide.

EXAMPLE 3

A further column of packed porous glass beads is prepared. "Glycohase" G beads are used and initially are reacted by 40° C. in dimethylformamide with tosyl chloride (10% by weight of beads) and one equivalent, to the chloride, of triethylamine. Thereafter the glass is filtered, washed and reacted with an excess of thioacetic acid to displace toxyl on the bead surface. The beads then are separated from the reaction medium and added to a vessel containing water in order to hydrolyze the acid and yield the thiol derivative thereof. Subsequently, the beads are reacted in water at 25° C. with mercaptosuccinic anhydride in order to obtain beads with the mixed disulfide immobilized on their surface. The mixed disulfide is an electrophylic reagent which has specific covalent reactivity for primary terminal amino groups.

Example 1 is then again repeated except that the column containing the immobilized disulfide replaces column 2 containing the immobilized aminopeptidase M. Rather than degrading unreacted chains, passage through this column serves to scavenge such chains by the covalent reaction between the disulfide and the free terminal amino group on unreacted chains. Therefore, the reaction solution which is recovered from the column has the unreacted polypeptide chain removed therefrom.

After each scavenging operation an aqueous solution (pH 8) of sodium borohydride (0.5 M) is passed through the column at 25° C. in order to remove the covalently bonded chains therefrom. The column is then reactivated by treatment with mercaptosuccinic anhydride to restore the disulfide bridge.

EXAMPLE 4

(C-Terminal Approach)

A. Preparation of Ethyl Ester Protected Amino Acids

The amino acids set forth in Example 2A are esterified by reaction with ethanol, under reflux, in the presence of a catalytic amount of anhydrous HCl. The reaction volume is concentrated and upon cooling the amino acid esters crystallize as hydrochlorides. These protected acids also are commercially available.

B. Preparation of Handle-First Amino Acid Complex

Poly U (10 mg) is treated with $NaIO_4$ (0.01 M) for 18 hours. The resulting dialdehyde is coupled to the spacer arm dipeptide, gly-L-arg, by reductive alkylation according to Royer, et al., *Biochem. and Biophys. Research Column.*, 64, 478 (1975).

The ethyl ester of valine is attached to the arginine carboxyl terminus of the handle via reaction in the presence of a water-soluble carbodiimide at pH6, 0°-4° C., 12 hours.

C. The Procedure

The basic reiterative procedure is the same as with respect to the N-terminal approach except that amino acid coupling is accomplished at pH 6 with ethyl dimethylaminopropyl carbodiimide HCl and deblocking and pruning of unreacted chains is accomplished using column 3 containing immobilized carboxypeptidase Y. For pruning, the pH is 5.5 in a phosphate buffer. For deblocking the pH of the solution, prior to passage through the column, is adjusted to 8.5 by addition of NaOH. In both instances a column and solution temperature of 35° C. is used. For separation and recovery of the peptide from the handle, successive passage through columns 4 and the column of Example 1B, is employed with the respective solutions being at a pH of 8 (using Tris) and using a solution and column temperatures of 35° C.

EXAMPLE 5

Synthesis of H-Leu-Phe-Leu-OH

A. Preparation of the Handle (PEG-CH₂CO-Gly-Arg(NO₂))

Polyethylene glycol (PEG) (14 g, Mol. Wt. 6000–7000) and potassium tert-butoxide (10 g) were dissolved in t-butanol (150 ml) by warming to 40° C. Ethyl bromoacetate (5 ml) was added over a period of 10 minutes. After an additional 2 hours of stirring at 40° C., the solvent was removed by a rotary evaporator. The residue was dissolved in 100 ml of 2 N NaOH and kept at room temperature for two hours. The pH of the mixture was then adjusted to 2.0. The PEG was extracted twice into 200 ml of $CHCl_3$. The organic extract was washed with water and then dried over $Na_2SO_4$. Evaporation of the solvent yielded 12 g of carboxymethyl-PEG.

Glycine was added to the carboxymethyl-PEG with a water-soluble carbodiimide as follows. Gly-OEt-Hcl (1.4 g) and carboxymethyl-PEG (3.4 g) were dissolved in 25 ml. of $H_2O$. The pH was adjusted to 6.0 with triethylamine. Ethyl dimethylaminopropyl carbodiimide HCl (EDC, 2 g) was added and pH was maintained at 6.0 with a pH-Stat. After 3 hours at room temperature, the reaction mixture was acidified to pH 2.0 and the product was extracted into $CHCl_3$. The organic layer was washed with 1 N HCl and water. After drying over $Na_2SO_4$ the solvent was evaporated under reduced pressure. The resulting PEG-CH₂CO-Gly-OEt (3.2 g) was dissolved in 20 ml of water and the pH adjusted to 10.5. The saponification was followed at this pH using a pH-stat. The titrant was 0.1 N NaOH. About 4 ml of base was consumed over the reaction period of one hour. Acidification and extraction with $CHCl_3$ gave 3.3 g of product. Amino acid analysis showed 100 moles of glycin/mg polymer.

Arg(NO₂)OMe HCl was reacted in a manner analogous to the coupling of glycine ethyl-ester. PEG-Gly-Arg(NO₂)OMe (3.3 g) was treated at pH 8.5 with 25 units of CPY immobilized on CL-Sepharose (liberatore, et al., (1976) FEBS Letters 68, 45). The pH was maintained with 0.1 N NaOH for 5 hours at room temperature. The bound enzyme was removed by filtration.

B. Preparation of PEG-CH₂COGly-Arg(NO₂)Leu-Phe-Leu-OH

Leu-OEt, Phe-OEt, and Leu-OET were added successively as described above using EDC mediated coupling and CPY deprotection. The rate of deprotection improved dramatically as the chain length increased. The amino acid analysis for the final peptide was in agreement with theory.

C. Release of the Peptide

A portion of the final product (1 g) was dissolved in 20 ml of MeOH/cyclohexene (1:1). Freshly prepared palladium black (250 mg) was added and the reaction mixture was stirred with refluxing for 1 hour to remove the nitro group on Arg. The catalyst was filtered and the product was dried in vacuo (0.9 g yield). The product was dissolved in 0.1 N-ethylmorpholineacetate buffer at pH 8.0 and bound trypsin (1 g, prepared acc. to Royer et al., Methods in Enzymol, (1977) 47, 40) was added. The suspension was tumbled for 6 hours. The release of the peptide was followed by TLC using authentic H-Leu-Phe-Leu-OH as a standard. The yield of product was 80%, based on the number of initiation sites available on the PEG handle.

EXAMPLE 6

This example illustrates the preparation of the tetrapeptide, Ala-Ala-Cys(ACM)-Lys(CBZ)-OH, which is the segment representing the first four residues of an active somatostatin analogue. Currently, this method of peptide synthesis is preferred. The handle used is PEG-CH₂CO-Gly-Met-OH. An advantage of this handle is that release of the target peptide can be achieved in one step using cyanogen bromide cleavage at the carboxyl side of Met at 30° C.

The handle is prepared as in Example 5 except that Met-OEt is used instead of the nitro-arginine acid ester and deblocking of the methionine ester is accomplished for four hours. EDC mediated coupling of the ethyl esters of Ala, Ala, Cys(ACM), and Lys(CBZ) was accomplished as described in Example 5. Deblocking was also effected in a similar fashion using CPY and the following times: 1st Ala-2 hours, 2nd Ala-1 hour, Cys-(ACM)-4 hours, Lys(CBZ)-4 hours.

After deblocking of Lys(CBZ)-OEt, the target peptide with the handle attached is dissolved in water containing a 100 fold excess of cyanogen bromide dispensed from a stock solution in acetonitrile (1 mg/ml). After 1 hour at room temperature, the mixture is lyophilized.

The target peptide is then recovered by ion exchange chromatography.

The procedures illustrated in the foregoing examples are easy to accomplish, readily susceptible to automation, and applicable to the aqueous, synthetic preparation of polypeptides from amino acids containing primary amino groups in the alpha position. As is well recognized, this includes all of the amino acids except proline and any analogs thereof. With respect to proline, the acylable amino group is a secondary amine and is not amenable to blocking and deblocking with the pyrrolidonecarboxyl group.

Accordingly, when the polypeptide being fashioned is to contain the proline residue and when an N-terminal route is used, it is necessary to block this acid by conventional techniques, such as with the carbobenzoxy (Z) group, and thereafter accomplish deblocking with, for example, HBr-glacial acetic acid. Therefore, in synthesizing a proline-containing polypeptide from the N-terminal, the above described procedure is interrupted after the blocked-proline is added to the chain. The chain can then be released from the handle, isolated and the blocking group removed. The chain then is reattached to the handle and the procedure described herein reiterated for the addition of subsequent acids onto the chain.

While several of the foregoing examples have particularly illustrated a method for preparing polypeptides utilizing the preferred aspects of the present invention in combination, it should be appreciated that many of the features utilized have general applicability outside of the specific procedures illustrated, both as concerns polymer synthesis and other multi-stage molecular transformation procedures involving sequential chemical reactions. For example, the manner of eliminating problems associated with incomplete precursor reaction by pruning is applicable to any multi-stage molecular transformation procedure where the unreacted precursor can be enzymaticably degraded or scavenged. The same is true for the enzymatic deblocking aspect described herein so long as the procedure requires a removable blocking group.

Thus, with respect to conventional solid phase peptide preparation wherein chain elongation is effected with the chain covalently affixed to an insoluble support, it will be appreciated that appropriate enzymatic solutions can be successively passed over the support to remove unreacted chains and to deblock at each stage of reiterative procedure. As to conventional solution methods in organic solvents, the use of immobilized enzymes as illustrated herein can, for example, be conveniently employed by simply isolating the peptide chain population after each sequential acid reaction and dissolving it in an aqueous medium.

Also, it will be appreciated that the feature of reversible coupling described herein has applicability beyond the reiterative procedure exemplified. It is generally applicable to multi-stage, molecular transformation procedures wherein, after chemical reaction of a transformable precursor, it is necessary to separate the transformed product from unreacted added compound. While particularly applicable to reiterative polymer synthesis, as with the other features, reversible coupling also can be employed in other multi-stage, molecular transformation procedures designed to construct compounds by sequential chemical reactions.

More particularly with respect to polymer synthesis, rather than for separation in the manner specifically exemplified, the handle on the growing chain can be used to couple the chain to an insoluble support during reaction with the desired added segment and during separation. Thus, a solid phase procedure can be utilized for chain elongation. Particular advantages envisioned are that the reaction can be accomplished in aqueous medium and the chain can be easily separated from the support after ultimate completion of the chain, or at any intermediate stage, without the necessity of using harsh conditions.

Accordingly, while the present invention has been described in connection with certain preferred embodiments, it is to be understood that it is not to be limited to only those embodiments disclosed. On the contrary, it is intended to cover all modifications and alternatives falling within the spirit and scope of the invention as expressed in the appended claims.

I claim:

1. A process for synthesizing a peptide chain having a distinct sequence of amino acid segments which comprises reacting, in an aqueous medium, a pure precursor containing a first amino acid segment of the peptide chain to be prepared having a free terminal carboxyl group or a free terminal amino group, with a second amino acid segment containing a free $N\alpha$-amino group and a blocked carboxyl group susceptible to enzymatic hydrolysis when the precursor has a free terminal carboxyl group or a free carboxyl group and a blocked $N\alpha$-amino group susceptible to enzymatic hydrolysis when the precursor has a free terminal amino group, deblocking the product peptide enzymatically, and then repeating the process of reaction and enzymatic deblocking until the desired peptide chain is prepared.

2. The process of claim 1 wherein the precursor contains a first amino acid segment covalently bonded to a polynucleotide handle.

3. The process of claim 1 wherein the precursor contains a first amino acid segment attached to a polyethylene glycol handle.

4. The process of claims 1, 2, or 3 wherein the second amino acid segment contains a blocked carboxyl group and the blocking group is an ester group.

5. The process of claim 4 wherein the ester group is an alkyl ester group.

6. The process of claim 5 wherein the carboxyl group is deblocked enzymatically using an esterase.

7. The process of claim 6 wherein the carboxyl group is deblocked using carboxypeptidase Y at pH 8-9.

8. The process of claims 1, 2, or 3 wherein the second amino acid segment contains a blocked amino group and the blocking group is the L-pyrrolidonecarboxyl group.

9. The process of claim 8 wherein the amino group is deblocked using L-pyrrolidonecarboxylpeptidase.

10. A process for preparing a peptide chain having a distinct sequence of amino acid segments which comprises reacting a pure precursor containing a first amino acid segment of the peptide chain to be prepared having a free terminal carboxyl group or a free terminal amino group, with a second amino acid segment containing a free $N\alpha$-amino group and a blocked carboxyl group when the precursor has a free terminal carboxyl group or a free carboxyl group and a blocked $N\alpha$-amino group when the precursor has a free terminal amino group, in an aqueous medium; and removing unreacted precursor by enzymatic degradation or by scavenging.

11. The process of claim 10 wherein the precursor complex contains a free terminal carboxyl group and the unreacted complex is removed by enzymatic degradation using carboxypeptidase Y at pH 5 to 6.

12. The process of claim 10 wherein the precursor complex contains a free terminal amino group and the unreacted complex is removed by enzymatic degradation using aminopeptidase M.

* * * * *